United States Patent
Na et al.

(10) Patent No.: US 10,548,507 B2
(45) Date of Patent: Feb. 4, 2020

(54) BIOLOGICAL BRAIN AGE CALCULATION DEVICE AND CALCULATION METHOD THEREFOR

(71) Applicants: SAMSUNG LIFE PUBLIC WELFARE FOUNDATION, Seoul (KR); INDUSTRY-ACADEMIC COOPERATION FOUNDATION, YONSEI UNIVERSITY, Seoul (KR)

(72) Inventors: Duk L. Na, Seoul (KR); Sang Won Seo, Seoul (KR); Jun Kyung Seong, Seoul (KR); Changsoo Kim, Seoul (KR)

(73) Assignees: SAMSUNG LIFE PUBLIC WELFARE FOUNDATION, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 291 days.

(21) Appl. No.: 15/315,443

(22) PCT Filed: Jun. 3, 2015

(86) PCT No.: PCT/KR2015/005564
§ 371 (c)(1),
(2) Date: Dec. 1, 2016

(87) PCT Pub. No.: WO2015/186963
PCT Pub. Date: Dec. 10, 2015

(65) Prior Publication Data
US 2017/0095180 A1 Apr. 6, 2017

(30) Foreign Application Priority Data
Jun. 3, 2014 (KR) ........................ 10-2014-0067742

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *A61B 5/107* (2013.01); *A61B 5/1075* (2013.01);
(Continued)

(58) Field of Classification Search
None
See application file for complete search history.

(56) References Cited

U.S. PATENT DOCUMENTS

| 6,269,339 B1 * | 7/2001 | Silver ................. G06F 19/3456 705/2 |
| 2011/0129129 A1 | 6/2011 | Avinash et al. |

(Continued)

FOREIGN PATENT DOCUMENTS

| GB | 2491027 A | 11/2012 |
| JP | 2002-209867 A | 7/2002 |

(Continued)

OTHER PUBLICATIONS

Office action dated Dec. 5, 2017 from Japan Intellectual Property Office in a counterpart Japanese Patent Application No. 2016-570992 (English translation is submitted herewith).

(Continued)

*Primary Examiner* — Jonathan Cwern
(74) *Attorney, Agent, or Firm* — The PL Law Group, PLLC

(57) ABSTRACT

A biological brain age is calculated by measuring a brain cortex thickness of each region in a brain MRI image of a person to be examined, and comparing the measured brain cortex thickness with normal control group information. A (Continued)

device for calculating the biological brain includes an image information input unit to input an MRI brain image of a person to be examined, a brain age calculation control unit to control a biological brain age calculation operation of the person to be examined based on the MRI brain image, a brain thickness measuring unit to measure a brain cortex thickness of each region in the MRI brain image, and a brain age calculating unit to match the measured brain cortex thickness with a normal range of brain thickness of each age, and calculate a biological brain age of the person to be examined.

5 Claims, 8 Drawing Sheets

(51) Int. Cl.
  *G16H 10/20* (2018.01)
  *G16H 30/40* (2018.01)
  *A61B 5/107* (2006.01)
  *G16H 50/20* (2018.01)

(52) U.S. Cl.
  CPC .......... *A61B 5/1076* (2013.01); *A61B 5/4064* (2013.01); *A61B 5/7275* (2013.01); *A61B 5/7278* (2013.01); *A61B 5/742* (2013.01); *G16H 10/20* (2018.01); *G16H 30/40* (2018.01); *G16H 50/20* (2018.01); *A61B 2576/023* (2013.01); *A61B 2576/026* (2013.01)

(56) References Cited

U.S. PATENT DOCUMENTS

| | | | |
|---|---|---|---|
| 2012/0296194 A1 | 11/2012 | Sherlock Au et al. | |
| 2013/0217976 A1* | 8/2013 | Heniford | A61B 5/4848 600/300 |
| 2016/0155226 A1* | 6/2016 | Kano | A61B 5/055 382/131 |

FOREIGN PATENT DOCUMENTS

| | | |
|---|---|---|
| JP | 2003-132143 A | 5/2003 |
| JP | 2010-240290 A | 10/2010 |
| KR | 10-2008-0013829 A | 2/2008 |
| KR | 10-2011-0028443 A | 3/2011 |
| KR | 10-2011-0108873 A | 10/2011 |
| KR | 10-1203047 B1 | 11/2012 |
| KR | 10-2014-0063809 A | 5/2014 |

OTHER PUBLICATIONS

European Search Report for EP15802511.4 from European patent office in a counterpart European patent application.
Herve Lemaitre, "Normal age-related brain morphometric changes: nonuniformity across cortical thickness, surface area and gray matter volume?", Neurobiology of Aging, vol. 33, 617.e1-617.e9.
Christian K. Tamnes et al., "Brain Maturation in Adolescence and Young Adulthood: Regional Age-Related Changes in Cortical Thickness and White Matter Volume and Microstructure", Cerebral Cortex, vol. 20, pp. 534-548, 2010.
Brandon A. Zielinski et al., "Longitudinal changes in cortical thickness in autism and typical development", Brain, vol. 137, p. 1799-1812, 2014.
International Search Report for PCT/KR2015/005564.

* cited by examiner

BRAIN HEALTH RESULT

| NAME | GENDER | AGE | EXAMINATION DATE |
|---|---|---|---|
|  | MALE | 55 |  |

| RESULT |
|---|
| ● YOUR BIOLOGICAL BRAIN AGE IS 60.<br>● A FACTOR INCREASING YOUR BIOLOGICAL BRAIN AGE IS SMALL WEIGHT AND DRINKING HABIT.<br>● IN ORDER TO MAINTAIN GOOD BRAIN STATE, IT IS ADVISED YOU TO FOLLOW THE FOLLOWINGS. |

| LIST | VALUE | NORMAL RANGE |
|---|---|---|
|  |  |  |
|  |  |  |
|  |  |  |
|  |  |  |

BIOLOGICAL BRAIN AGE CALCULATION DEVICE AND CALCULATION METHOD THEREFOR

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/005564, filed Jun. 3, 2015, which claims priority to the benefit of Korean Patent Application No. 10-2014-0067742 filed in the Korean Intellectual Property Office on Jun. 3, 2014, the entire contents of which are incorporated herein by reference.

TECHNICAL FIELD

The present invention relates to a technology for calculating a biological brain age, and more particularly, to a device and a method for calculating a biological brain age by measuring a brain cortex thickness of each region in a brain MRI image of a person to be examined, and comparing the measured brain cortex thickness with normal control group information.

BACKGROUND ART

In general, a technology for presenting particular quantitative information about a brain image has been disclosed. However, the related art is mainly for the purpose of research, and is used by using an average value of a use group, and a method of quantitatively presenting brain atrophy information of an individual brain in a dimension of a health examination to each person has not been carried on up to now.

When a current brain disease is not found even though an MRI is taken during a health examination, information on a current health state of a brain is not provided to a person to be examined, so that there is a problem in that quantitative information is particularly transmitted to a user.

For example, a numerical value of a result of a blood test, a urine test, and the like compared to a normal numerical value is presented to the user, so that the user can use the result, but a standardized index about a brain index does not exist.

Further, a diagnosis of a patient depends on a qualitative determination of a photographed image, rather than a particular index, so that during the health examination, quantitative information about a current health state of a brain or a future brain disease of a patient has not provided at all.

SUMMARY

The present invention is suggested for solving the problem in the related art, and an object of the present invention is to provide a device for calculating a biological brain age, which measures a brain cortex thickness of each region in an MRI brain image of a person to be examined, calculates a biological brain age of the person to be examined according to the measured thickness of the brain cortex, and provides the biological brain age in a form of a mathematical index.

Another object of the present invention is to provide a device for calculating a biological brain age, which further includes a brain age information unit, and stores and manages brain thickness information for each age, brain disease characteristic information, basic information of a person to be examined, MRI brain image information, and health questionnaire information for calculating a brain age.

Another object of the present invention is to provide a device for calculating a biological brain age, which further includes a brain disease predicting unit, and predicts and provides specific brain disease information according to a brain age of a person to be examined.

Another object of the present invention is to provide a device for calculating a biological brain age, which draws a dangerous life habit factor according to predicted specific brain disease information of each person to be examined, and provide life guideline information for prevention.

Another object of the present invention is to provide a method for calculating a biological brain age, which receives basic information, health questionnaire information, and an MRI brain image of a person to be examined, measures information on a brain cortex thickness of each region, and calculates and provides a brain age of the person to be examined.

Another object of the present invention is to provide a method for calculating a biological brain age, in which a brain cortex thickness of a person to be examined is applied to a regression equation, in which the degree of brain atrophy according to an age and a brain cortex thickness is applied by an estimation statistical method, when a brain age of the person to be examined is calculated.

A device for calculating a biological brain age according to the present invention includes: an image information input unit configured to input an MRI brain image of a person to be examined; a brain age calculation control unit configured to control a biological brain age calculation operation of the person to be examined based on the MRI brain image; a brain thickness measuring unit configured to measure a brain cortex thickness of each region in the MRI brain image; and a brain age calculating unit configured to match the measured brain cortex thickness with a normal range of brain thickness of each age, and calculate a biological brain age of the person to be examined.

The device may further include a brain age information unit connected with the brain age calculation control unit and configured to store at least one element of information among brain thickness information of each age of a normal control group, brain thickness invasion region information for each brain disease, basic information about the person to be examined, MRI brain image information of the person to be examined, and health questionnaire information of the person to be examined.

The device may further include a person to be examined information input unit connected with the brain age calculation control unit, and configured to input basic information and health questionnaire information of the person to be examined.

The device may further include a brain disease predicting unit connected with the brain age calculation control unit, and configured to provide predicted specific brain disease information according to a brain age of the person to be examined calculated by the brain age calculating unit.

The brain disease predicting unit may draw an individual life habit factor causing aggregation of a brain thickness in the health questionnaire of the person to be examined according to the predicted specific brain disease information, and provide life guidance information for preventing a specific brain disease.

A method of calculating a biological brain age according to the present invention includes: (a) inputting basic information and health questionnaire information of a person to be examined by using a person to be examined information input unit; (b) inputting an MRI brain image of the person to be examined by using an image information input unit; (c) measuring a brain cortex thickness of each region in the MRI brain image by using a brain thickness measuring unit; and (d) matching the measured brain cortex thickness with a normal range of brain thickness of each age, and calculating a biological brain age of the person to be examined by using the brain age calculating unit.

As described above, the biological brain age calculating device according to the present invention measures a brain cortex thickness of each region in an MRI brain image of a person to be examined, and calculates a biological brain age of the person to be examined according to the measured brain cortex thickness in a form of a mathematical index, thereby accurately providing a brain health state to the person to be examined during the health examination, and further preventing a brain disease by utilizing the biological brain age in an early examination of the brain health.

Further, it is possible to systematically manage brain thickness information for each age, brain disease characteristic information, basic information of a person to be examined, MRI brain image information, and health questionnaire information for calculating a brain age.

Further, it is possible to alert a person to be examined for a future developable brain disease according to a current brain thickness and help the person to be examined to make an effort to prevent the brain disease by predicting specific brain disease information according to a brain age of the person to be examined.

Further, it is possible to help a person to be examined to actively improve a life habit for preventing a brain disease by drawing a risk life habit factor according to predicted specific brain disease information and providing life guidance information for preventing the brain disease for each person to be examined.

The biological brain age calculating method according to the present invention may calculate and provide a biological brain age of a person to be examined and predict a regenerative brain disease and provide diagnosis information during a health examination by receiving basic information, health questionnaire information, and an MRI brain image of the person to be examined and measuring brain cortex thickness information of each region.

In the calculation of a brain age of a person to be examined, it is possible to accurately calculate a brain age by applying a brain cortex thickness of the person to be examined to a regression equation, in which the degree of brain atrophy according to an age and a brain cortex thickness is applied by a prediction statistical method, and consulting an accurate brain health state based on the calculated brain age data.

DETAILED DESCRIPTION

Hereinafter, particular contents for carrying out a biological brain age calculating device and method according to the present invention will be described below.

Figure 1:
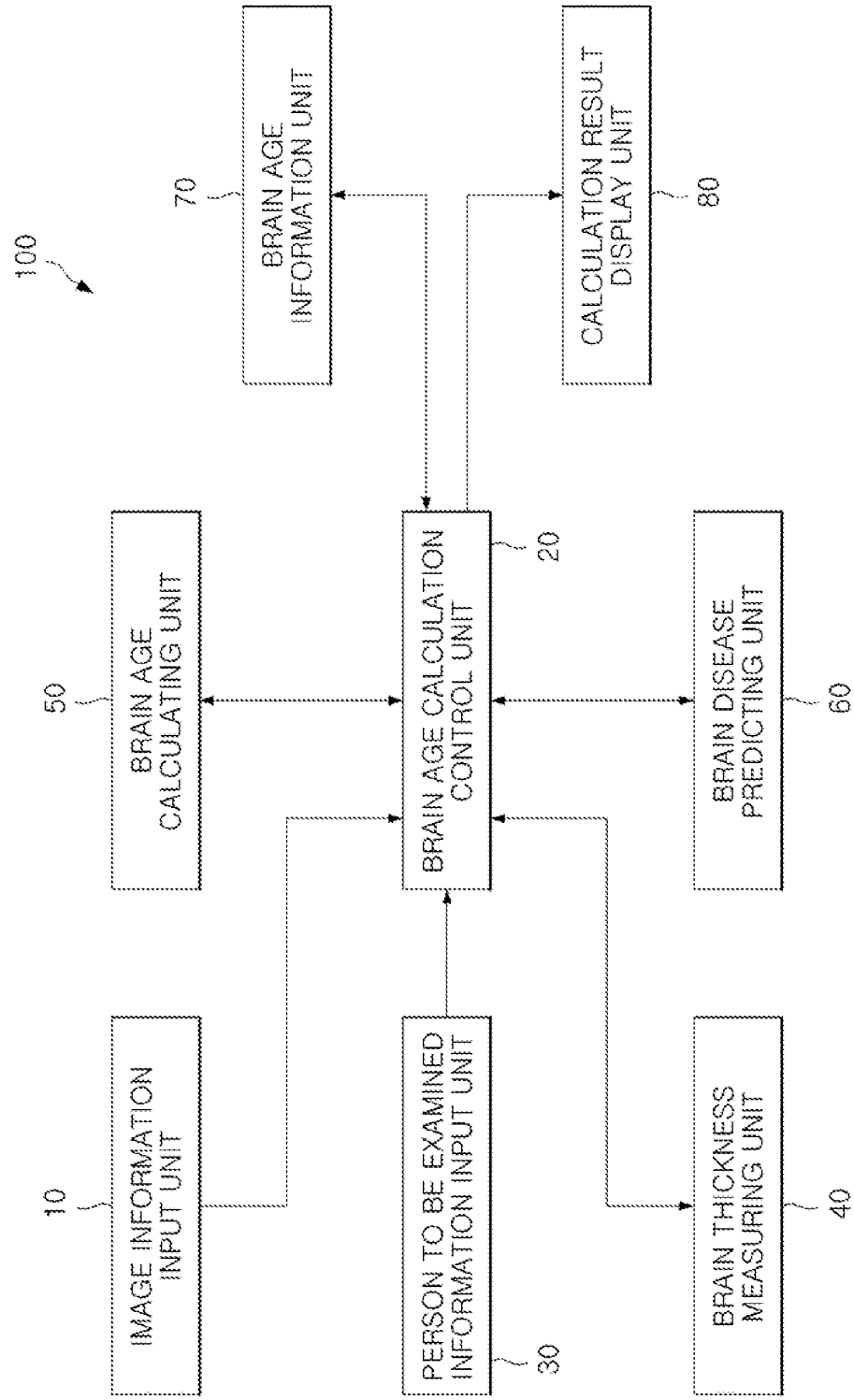
FIG. 1 is a diagram illustrating an entire configuration of a biological brain age calculating device according to the present invention.

FIG. 1 is a diagram illustrating an entire configuration of a biological brain age calculating device according to the present invention, and includes an image information input unit 10, a brain age calculation control unit 20, a person to be examined information input unit 30, a brain thickness measuring unit 40, a brain age calculating unit 50, a brain disease predicting unit 60, a brain age information unit 70, and a calculation result display unit 80.

The image information input unit 10 inputs an MRI brain image of a person to be examined, an image, through which a cortex state of each region of a brain of the person to be examined may be confirmed, may be input as the MRI brain image according to the present invention, and the MRI brain image information input by the image information input unit 10 is transmitted to the brain age calculation control unit 20.

The brain age calculation control unit 20 controls a biological brain age calculating operation of the person to be examined based on the MRI brain image, receives the MRI brain image information, and requests a brain cortex thickness calculating operation of each region from the brain thickness measuring unit 40.

The person to be examined information input unit 30 is connected with the brain age calculation control unit 20 and inputs basic information and health questionnaire information of the person to be examined, and the person to be examined of the MRI brain image input through the person to be examined information input unit 30 may be identified, and the health questionnaire information written by the person to be examined may be utilized for future incurable brain disease information.

In the present invention, the basic information includes at least one of a name, an age, a gender, an BMI, a medical insurance card number, and education information of the person to be examined, and the health questionnaire information refers to information, based on which it is possible to confirm a current health state including a usual life habit or a past disease name of the person to be examined.

The brain thickness measuring unit 40 may be connected with the brain age calculating control unit 20 to measure a brain cortex thickness of each region in the MRI brain image, and calculate an entire average brain thickness and a brain thickness of each region of the person to be examined, and transmit the calculated entire average brain thickness and brain thickness of each region to the brain age calculation control unit 20.

The brain age calculating unit 50 is connected with the brain age calculation control unit 20, and matches the measured thickness of the brain cortex with a normal range of a brain thickness of each age, and calculates a biological brain age of the person to be examined, and in the present invention, the brain age calculating unit 50 calculates a brain age of the person to be examined by applying the brain cortex thickness of the person to be examined to a regression equation, in which the degree of brain atrophy according to an age and a brain cortex thickness is applied by a prediction statistical method.

Figure 2A:
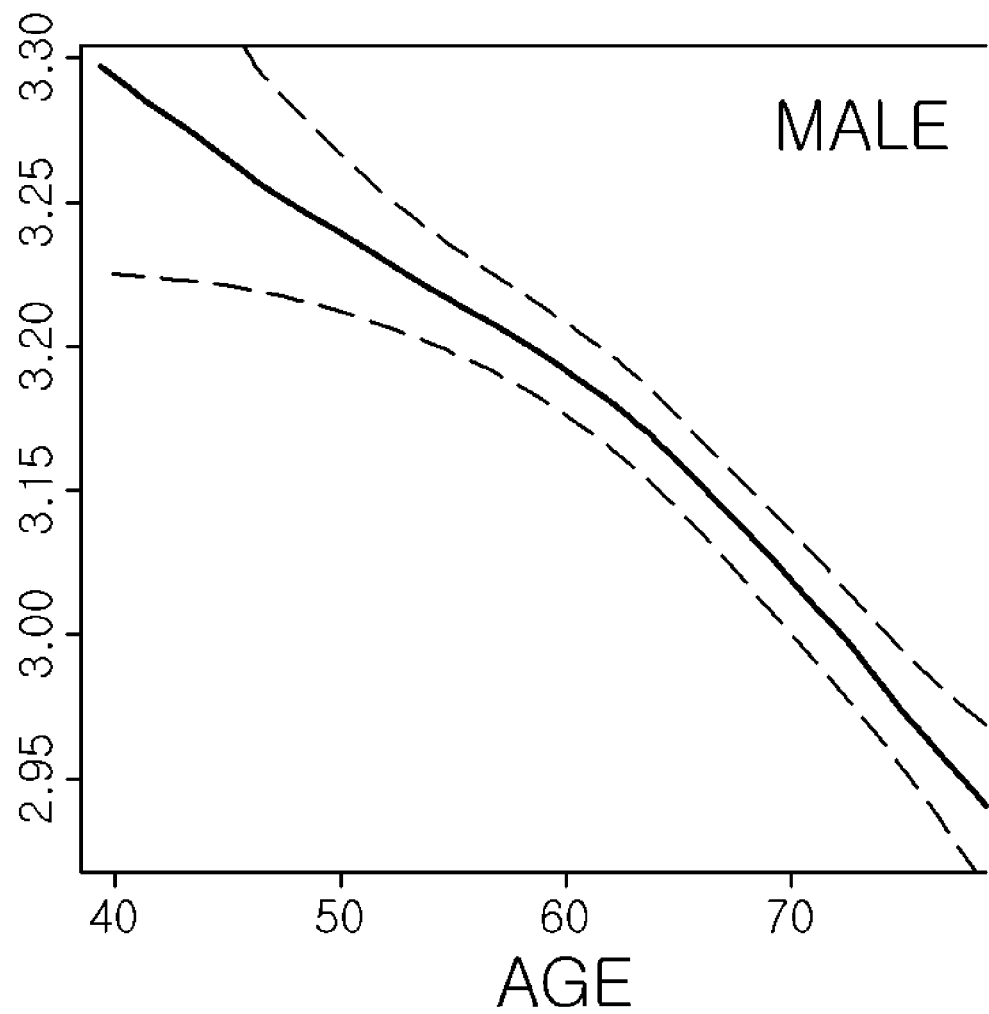
FIGS. 2A, 2B and 2C are diagrams illustrating a relation between an age and a brain cortex thickness according to a male, a female, and both genders in calculating a biological brain age according to the present invention.
Figure 2B:
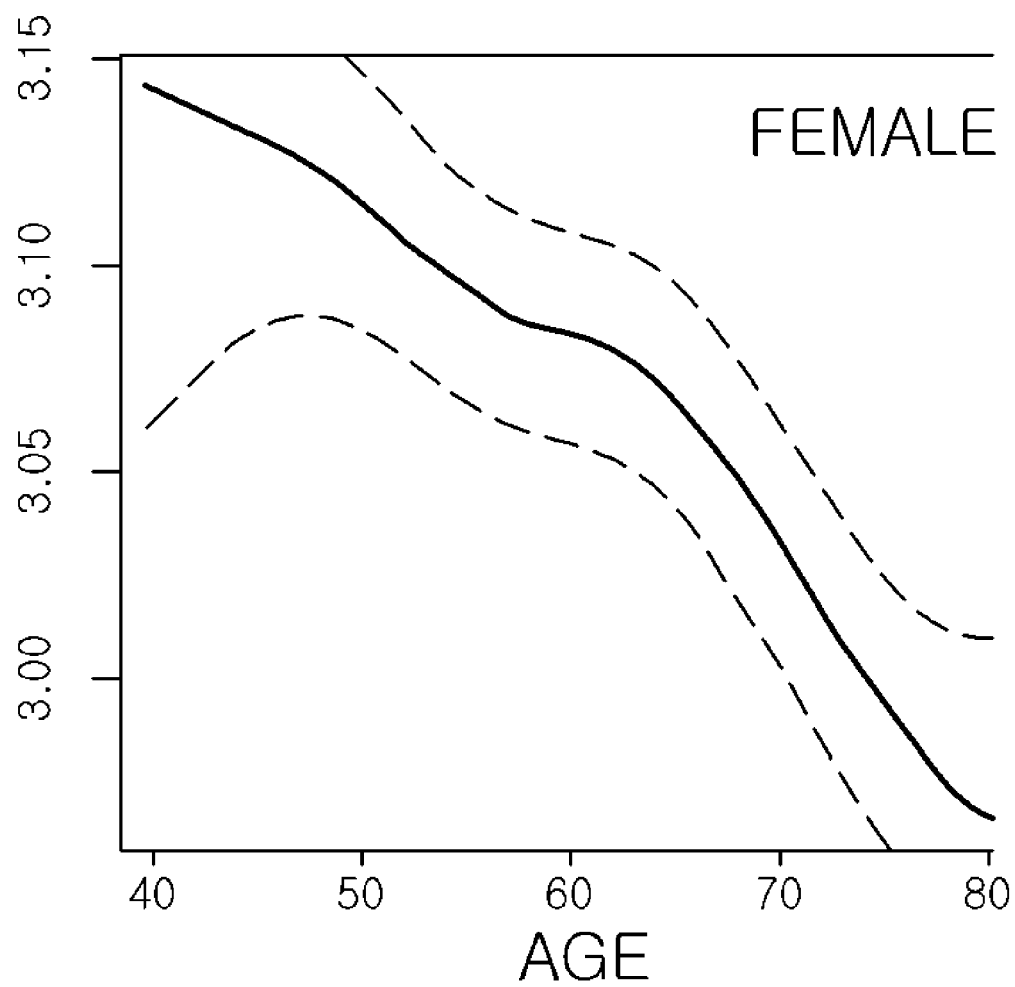
Figure 2C:
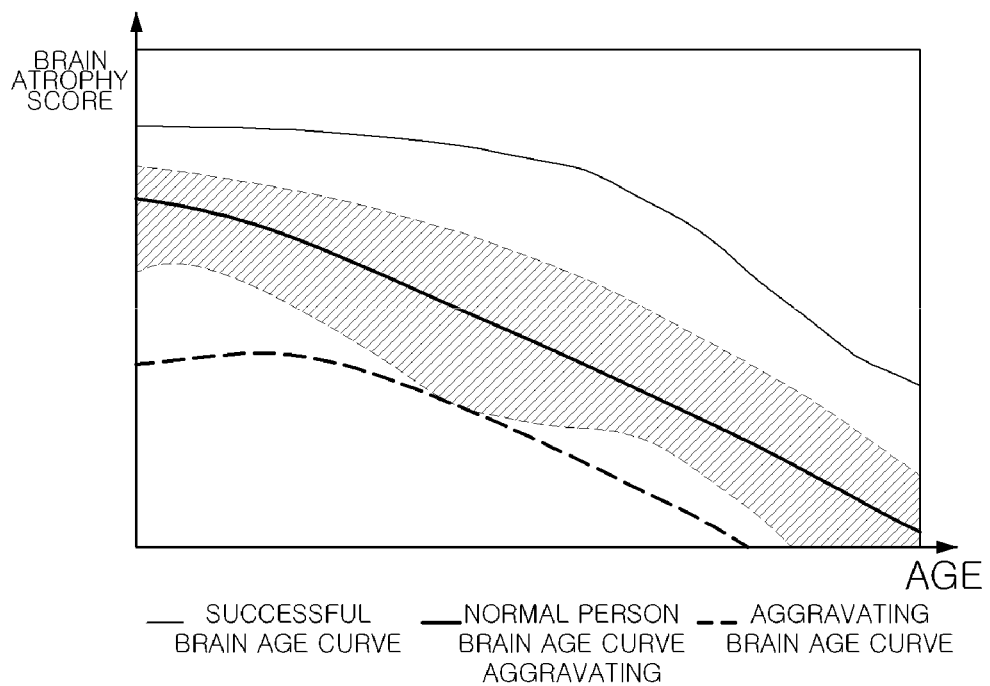

That is, the present invention may photograph an MRI of a subject of a normal control group for each age, calculates an average brain thickness and a brain thickness of each region, and calculate a brain thickness of each age of the normal control group, and in the exemplary embodiment of the present invention, the graph of FIG. 2C may be drawn with an average brain thickness value of a total of 2,500 subjects, and thus, average brain thickness information according to a gender may be drawn as illustrated in FIGS. 2A and 2B.

The brain disease predicting unit 60 is connected with the brain age calculation control unit 20, and provides specific brain disease information predicted according to the brain age of the person to be examined calculated by the brain age calculating unit.

Figure 3:
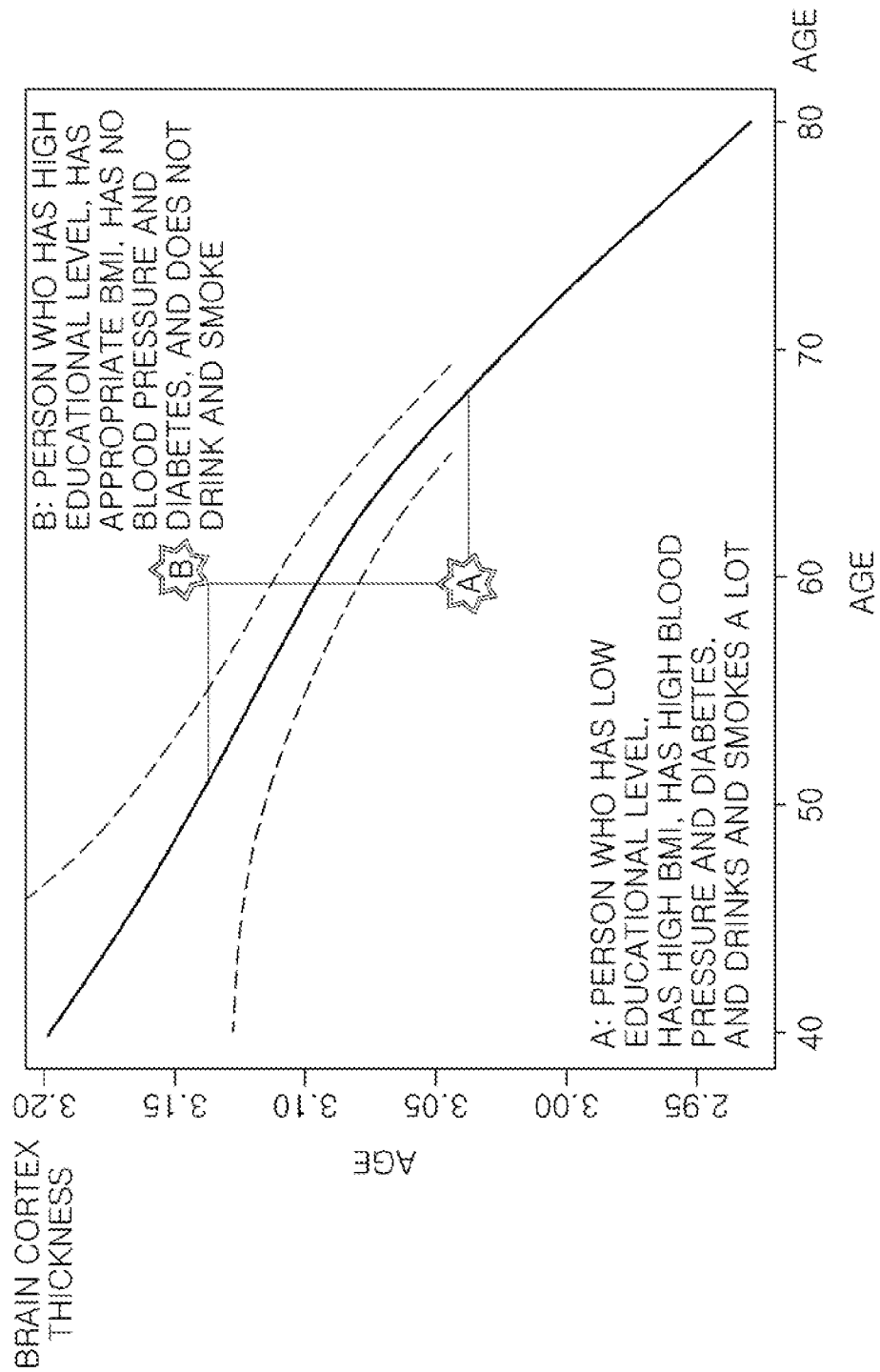
FIG. 3 is a diagram illustrating an exemplary embodiment of calculating a brain age of each person in a relation between an age and a brain cortex thickness in the biological brain age calculating device according to the present invention.

That is, in the present invention, a brain age is calculated by matching to an age of the normal control group and the information on the brain cortex thickness as illustrated in FIG. 3, and when person A who has a small numerical value of a brain thickness is compared with person B who has the same age as that of person A and has a large numerical value of a brain thickness, it is confirmed that person A has a low educational level, has a high BMI, high blood pressure and diabetes, and smokes and drinks a lot, and person B has a high educational level, has an appropriate BMI, has no high blood pressure and diabetes, and does not smoke and drink through the health questionnaire information, and developable degenerative brain disease information according to the current degree of brain atrophy may be provided.

As described above, the brain disease predicting unit 60 may draw an individual life habit factor causing aggregation of a brain thickness in the health questionnaire of the person to be examined according to the predicted specific brain disease information, and provide life guidance information for preventing a specific brain disease through the calculation result display unit 80.

Figure 4:
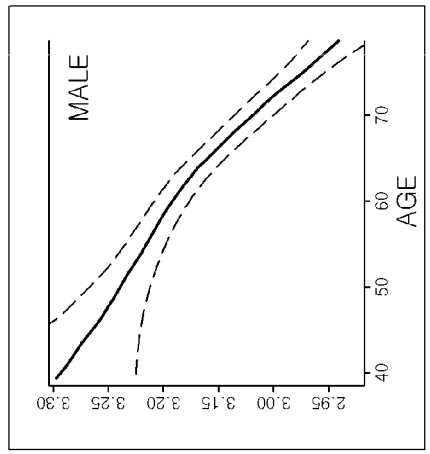
FIG. 4 is a diagram illustrating an exemplary embodiment of a calculation result display unit in the biological brain age calculating device according to the present invention.

The calculation result display unit 80 is connected with the brain age calculation control unit 20 and displays a process of calculating the brain age of the person to be examined to the outside, and in the exemplary embodiment of the present invention, as illustrated in FIG. 4, the calculation result display unit 80 displays a name, a gender, an age, and an examination date which are the basic information of the person to be examined, and displays the brain age calculation result and the brain disease prediction information.

Further, the calculation result display unit 80 may report numerical value information on a biological brain age for the examination result, present a factor related to the brain age for consideration of the life habit and a possible risk factor and a protective factor customized to a person, and inform a numerical value getting out of the normal range.

That is, like the exemplary embodiment of the present invention, for the person who has low weight light and drinks a lot, the present invention enables the person to be examined to more easily understand his/her brain age calculation result with the phrase "Your current brain age is 60, and is older than your actual age of 55 by five years. A highly possible factor causing aging of your brain age is low weight and a heavy drinking habit.

The brain age information unit 70 is connected with the brain age calculation control unit 20, and stores at least one element of information among brain thickness information of each age, each gender, and each educational level of the normal control group, brain thickness invasion region information for each brain disease, basic information about the person to be examined, MRI brain image information of the person to be examined, and the health questionnaire information of the person to be examined.

As described above, the biological brain age calculating device according to the present invention measures a brain cortex thickness of each region in an MRI brain image of a person to be examined, and calculates a biological brain age of the person to be examined according to the measured brain cortex thickness in a form of a mathematical index, thereby accurately providing a brain health state to the person to be examined during the health examination, and further preventing a brain disease by utilizing the biological brain age in an early examination of the brain health.

Figure 5:
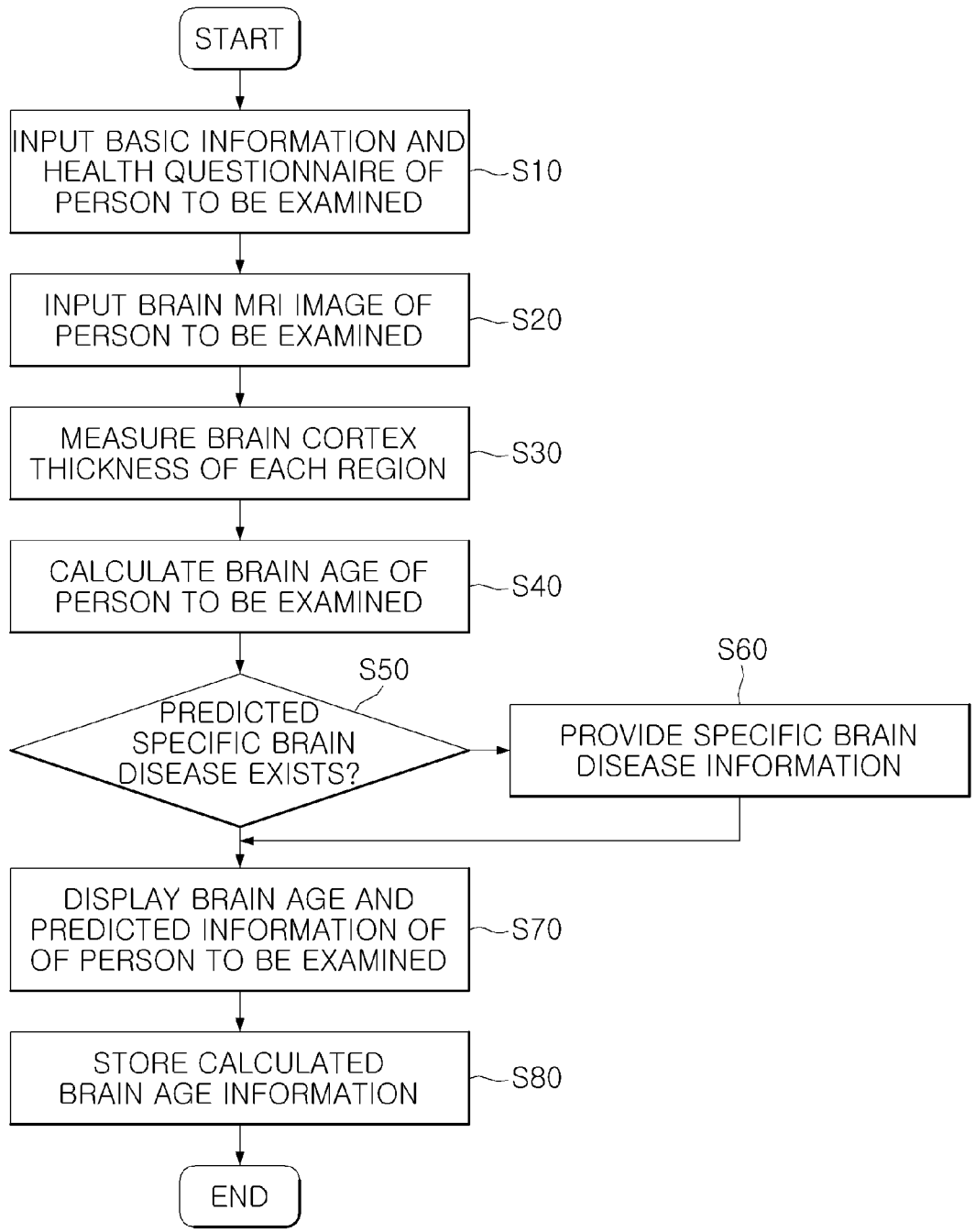
FIG. 5 is a flowchart illustrating an entire flow of a biological brain age calculating method according to the present invention.

FIG. 5 is a flowchart illustrating an entire flow of a biological brain age calculating method according to the present invention, operation S10 of inputting basic information and health questionnaire information of the person to be examined is performed by using the person to be examined information input unit 30, and in the exemplary embodiment of the present invention, and the basic information input in operation S10 includes at least one of a name, an age, a gender, an BMI, a medical insurance card number, and education information of the person to be examined, and the health questionnaire information refers to information, based on which it is possible to confirm a current health state including a usual life habit or a past disease name of the person to be examined.

In the biological brain age calculating method according to the present invention, although not illustrated in the drawing, an operation of storing brain thickness information of each age, each gender, and each educational level of the normal control group, and brain thickness invasion region information of each brain disease in the brain age information unit is preceded.

Next, operation S20 of inputting an MRI brain image of a person to be examined is performed by using the image information input unit 10, operation S30 of measuring a brain cortex thickness of each region in the MRI brain image is performed by using the brain thickness measuring unit 40, and operation S40 of calculating a biological brain age of the person to be examined by matching the measured brain cortex thickness and a normal range of brain thickness of each age is performed by using the brain age calculating unit 50.

In the present invention, operation S40 calculates a brain age of the person to be examined by applying the brain cortex thickness of the person to be examined to a regression equation, in which the degree of brain atrophy according to an age and a brain cortex thickness is applied by a prediction statistical method.

Next, operation S50 of determining whether future developable degenerative brain disease information exists on the basis of the brain age calculated in operation S40 and basic information and health questionnaire information of the person to be examined input in operation S10 is performed by using the brain disease predicting unit 60, and when the regenerative brain disease information exists in operation S50, operation S60 of providing the predicted brain disease information is performed.

Figure 6:
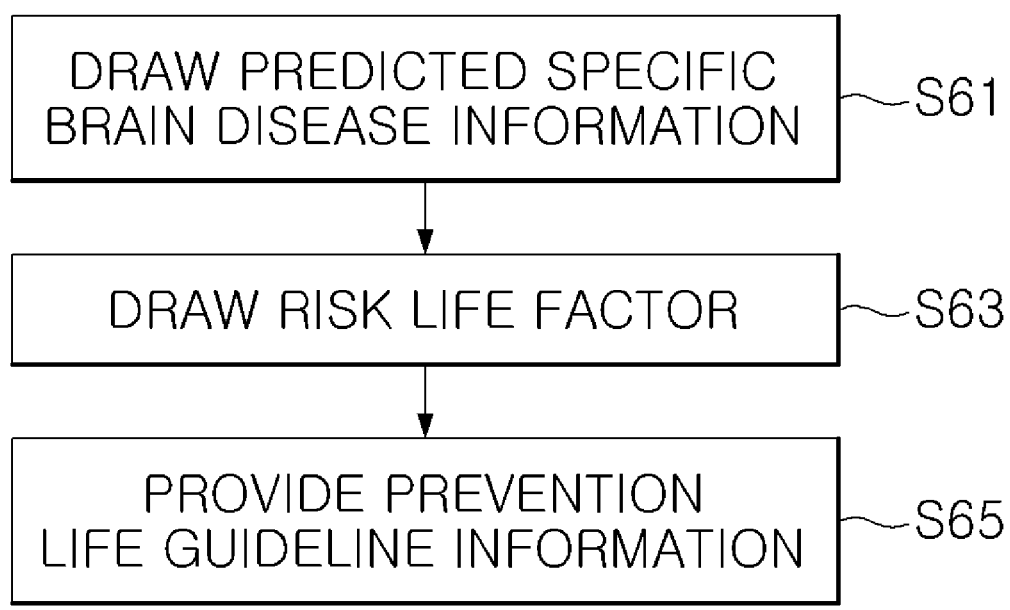
FIG. 6 is a flowchart illustrating a detailed flow of operation S60 in the biological brain age calculating method according to the present invention.

As illustrated in FIG. 6, operation S60 includes operation S61 of drawing predicted specific brain disease information, operation S63 of drawing an individual life habit factor causing aggravation of the brain thickness from the health questionnaire of the person to be examined according to the predicted specific brain disease information, and operation S65 of providing life guideline information for preventing the specific brain disease.

Next, operation S70 of displaying the calculated brain age of the person to be examined and the predicted specific brain disease information on the calculation result display unit 80 is performed, and operation S80 of storing the calculated brain age and the predicted specific brain disease information in the brain age information unit 70 is performed.

As described above, when the biological brain age calculating method according to the present invention is applied, it is possible to calculate and provide a biological brain age of a person to be examined and predict a regenerative brain disease and provide diagnosis information during a health examination by receiving basic information, health questionnaire information, and an MRI brain image of the person to be examined and measuring brain cortex thickness information of each region.

In the above, the exemplary embodiments of the present invention have been described, but the technical spirit of the present invention is not limited to the exemplary embodiments, and various biological brain age calculating devices and methods may be implemented within the scope of the technical spirit of the present invention.

The invention claimed is:

1. A device for calculating a biological brain age, comprising:
    a control unit to control a biological brain age calculation operation of a person to be examined based on a magnetic resonance imaging (MRI) brain image of the person to be examined by receiving the inputted MRI brain image of the person to be examined and requesting a brain thickness measurement;
    a storing unit connected with the control unit, the storing unit storing brain thickness information correlated with ages of a normal control group, brain thickness invasion region information for brain diseases, basic information comprising an age of the person to be examined, the MRI brain image information of the person to be examined, and health questionnaire information of the person to be examined;
    a processor comprising:
        a first input unit to input a magnetic resonance imaging (MRI) brain image of a person to be examined;
        a brain thickness measuring unit to receive the request of the brain thickness measurement from the control unit and measure a brain cortex thickness of each of predetermined regions in the MRI brain image;
        a brain age calculating unit to match the measured brain cortex thickness with the brain thickness information correlated with the ages of the normal control group, and calculate the biological brain age of the person to be examined only with the measured brain cortex thickness by applying the brain cortex thickness of the person to be examined to a regression equation using an estimation statistical method for modelling a degree of brain atrophy according to an age and a brain cortex thickness;
        a second input unit connected with the control unit, the second input unit to input basic information and health questionnaire information of the person to be examined; and
        a brain disease predicting unit connected with the control unit, the brain disease predicting unit to provide predicted specific brain disease information according to the biological brain age of the person to be examined calculated by the brain age calculating unit, wherein the brain disease predicting unit determines an individual life habit factor causing aggravation of a brain thickness in the health questionnaire of the person to be examined according to the predicted specific brain disease information, and provides life guidance information for preventing a specific brain disease.

2. The device of claim 1, further comprising:
    a displaying unit connected with the control unit, and configured to display the calculated biological brain age.

3. A method of calculating a biological brain age, comprising:
    storing brain thickness information of an age, a gender, and an educational level of a normal control group, and brain thickness invasion region information for brain diseases;
    obtaining basic information and health questionnaire information of a person to be examined, wherein the basic information and health questionnaire information includes an age of the person;
    obtaining an MRI image of a brain of the person to be examined;
    measuring brain cortex thicknesses of predetermined regions of the brain in the MRI image; and
    calculating a biological brain age of the person to be examined by applying the brain cortex thickness of the person to be examined to a regression equation using an estimation statistical method for modelling, a degree of brain atrophy according to an age and a brain cortex thickness; and
    providing predicted specific brain disease information according to the calculated biological brain age of the person to be examined, the providing of the predicted specific brain disease information comprising:
    determining an individual life habit factor causing aggravation of a brain thickness in the health questionnaire of the person to be examined according to the predicted specific brain disease information; and
    providing life guidance information for preventing a specific brain disease.

4. The method of claim 3, further comprising:
    displaying the calculated brain age and the predicted specific brain disease information of the person to be examined on a displaying unit after providing the predicted specific brain disease information; and
    storing the calculated brain age and the predicted specific brain disease information.

5. A device for calculating a biological brain age, consisting of:
    a control unit to control a biological brain age calculation operation of a person to be examined based on a magnetic resonance imaging (MRI) brain image by receiving the MRI brain image of the person to be examined and requesting a brain thickness measurement;
    a processor comprising:
        a first input unit to input a magnetic resonance imaging (MRI) brain image of a person to be examined;
        a brain thickness measuring unit to receive the request of the brain thickness measurement from the control unit and measure a brain cortex thickness of each of predetermined regions in the MRI brain image;
        a storing unit connected with the control unit, the storing unit storing brain thickness information correlated with ages of a normal control group, brain thickness invasion region information for brain diseases, basic information comprising an age of the person to be examined, MRI brain image information of the person to be examined, and health questionnaire information of the person to be examined;

a brain age calculating unit to match the measured brain cortex thickness with the brain thickness information correlated with the ages of the normal control group, and calculate the biological brain age of the person to be examined only with the measured brain cortex thickness by applying the brain cortex thickness of the person to be examined to a regression equation using an estimation statistical method for modelling a degree of brain atrophy according to an age and a brain cortex thickness; and a second input unit connected with the control unit, the second input unit to input basic information and health questionnaire information of the person to be examined;

a brain disease predicting unit connected with the control unit, the brain disease predicting unit to provide predicted specific brain disease information according to the biological brain age of the person to be examined calculated by the brain age calculating unit, wherein the brain disease predicting unit determines an individual life habit factor causing aggravation of a brain thickness in the health questionnaire of the person to be examined according to the predicted specific brain disease information, and provides life guidance information for preventing a specific brain disease; and a displaying unit connected with the control unit, and configured to display the calculated biological brain age.

* * * * *